(12) United States Patent
Tjin et al.

(10) Patent No.: US 8,158,363 B2
(45) Date of Patent: Apr. 17, 2012

(54) MICROFLUIDIC IMMUNOASSAY DEVICE

(75) Inventors: Swee Chuan Tjin, Singapore (SG); Rudi Irawan, Singapore (SG)

(73) Assignee: Nanyang Technological University, Singapore (SG)

( * ) Notice: Subject to any disclaimer, the term of this patent is extended or adjusted under 35 U.S.C. 154(b) by 597 days.

(21) Appl. No.: 12/282,166

(22) PCT Filed: Mar. 7, 2006

(86) PCT No.: PCT/SG2006/000044
§ 371 (c)(1),
(2), (4) Date: Sep. 8, 2008

(87) PCT Pub. No.: WO2007/102783
PCT Pub. Date: Sep. 13, 2007

(65) Prior Publication Data
US 2009/0194707 A1 Aug. 6, 2009

(51) Int. Cl.
*G01N 33/53* (2006.01)
(52) U.S. Cl. ............... 435/7.1; 435/283.1; 435/286.5; 435/287.2; 435/288.7; 436/518; 436/527; 427/2.11

(58) Field of Classification Search .................. None
See application file for complete search history.

(56) References Cited

U.S. PATENT DOCUMENTS

| | | | |
|---|---|---|---|
| 5,340,715 A * | 8/1994 | Slovacek et al. | 435/6.11 |
| 2001/0003043 A1* | 6/2001 | Metspalu et al. | 435/6 |
| 2002/0024662 A1 | 2/2002 | Ueno et al. | |
| 2002/0058273 A1* | 5/2002 | Shipwash | 435/6 |
| 2002/0072111 A1 | 6/2002 | Clarkin et al. | |
| 2002/0110839 A1* | 8/2002 | Bach et al. | 435/7.9 |
| 2003/0059853 A1* | 3/2003 | Lockhart | 435/7.9 |
| 2003/0157538 A1* | 8/2003 | Krull et al. | 435/6 |
| 2005/0274618 A1 | 12/2005 | Lee et al. | |

FOREIGN PATENT DOCUMENTS

| | | |
|---|---|---|
| EP | 1614465 A1 | 1/2006 |
| WO | WO 02/069016 A2 | 9/2002 |

* cited by examiner

Primary Examiner — N. C. Yang
(74) Attorney, Agent, or Firm — Knobbe Martens Olson & Bear LLP

(57) ABSTRACT

An optical fiber for use in an immunoassay device having at least one microfluidic channel, the optical fiber being for transmitting excitation light to the microfluidic channel and for transmitting emitted fluorescence to a light detector.

29 Claims, 4 Drawing Sheets

MICROFLUIDIC IMMUNOASSAY DEVICE

This application is U.S. National Phase of International Application PCT/SG2006/000044, filed Mar. 7, 2006 designating the U.S., and published in English as WO 2007/102783 on Sep. 13, 2007.

FIELD OF THE INVENTION

The invention relates to microfluidic devices, particularly to microfluidic fluorescence immunoassay devices.

BACKGROUND OF THE INVENTION

To improve the quality of healthcare, it is desirable that diagnostic tests such as immunoassays are quickly and inexpensively conducted at the point of care such as at home or by the hospital bed. To that end, microfluidic devices are ideal as they require only very small quantities of samples and reagents, thereby reducing cost and space.

Fluorescence methods in microfluidic immunoassay devices currently involve bulky optical detection systems that typically focus excitation light from an external light source onto a sample in a microchannel, and collect any fluorescence emitted with a set of complex lenses, mirrors and optical filters. As fluorescence emissions are isotropic, collection efficiency is generally low, usually less than 5%. Improving efficiency usually means needing a more complex, bigger and more expensive optical system. Alignment of the excitation light with the sample and the detection system is another challenge given the narrow channels in microfluidic device. This is exacerbated when excitation and collection is to be done along the length of the channel in order to obtain the total fluorescence emitted in a channel. Isotropic fluorescence emissions and scattered excitation light may also propagate through the microfluidic substrate and produce cross-talk in adjacent channels for multi-channel devices. Fluorescence background noise from the microfluidic substrate may even be higher than emissions produced by the samples.

SUMMARY

In accordance with a first preferred aspect there is provided an optical fibre for use in an immunoassay device having at least one microfluidic channel, the optical fibre being for transmitting excitation light to the microfluidic channel and for transmitting emitted fluorescence to a light detector.

The optical fibre may be for transmitting light to a light detector in a direction parallel with the direction of analyte flow.

In accordance with a second preferred aspect there is provided an optical fibre for use in an immunoassay device having at least one microfluidic channel, the optical fibre being for transmitting light to a light detector in a direction parallel with the general direction of analyte flow in the at least one microfluidic channel.

In accordance with a third preferred aspect there is provided an optical fibre for use in an immunoassay device having at least one microfluidic channel, the optical fibre forming at least a portion of a wall of the microfluidic channel.

In accordance with a fourth preferred aspect there is provided an optical fibre for use in an immunoassay device having at least one microfluidic channel, the optical fibre comprising at least one cavity, each cavity being adapted to retain analyte and for serving as a reaction chamber.

In accordance with a fifth preferred aspect there is provided an immunoassay device having at least one microfluidic channel, and at least one optical fibre, the optical fibre being for transmitting light to a light detector in a direction parallel with the general direction of analyte flow in the at least one microfluidic channel.

In accordance with a sixth preferred aspect there is provided an immunoassay device having at least one microfluidic channel, and at least one optical fibre, the optical fibre forming at least a portion of a wall of the microfluidic channel.

In accordance with a seventh preferred aspect there is provided an immunoassay device having at least one microfluidic channel, and at least one optical fibre, the optical fibre comprising at least one cavity, each cavity being adapted to retain analyte and for serving as a reaction chamber.

In accordance with a eighth preferred aspect there is provided an immunoassay device having at least one microfluidic channel, and at least one optical fibre, the optical fibre being for transmitting excitation light to the microfluidic channel and for transmitting emitted fluorescence to a light detector.

For the first, second, fifth and sixth aspects, the optical fibre may form at least a portion of a wall of the at least one microfluidic channel.

For the first, second, third, fifth, sixth and seventh aspects, the optical fibre may comprise at least one cavity, each cavity being adapted to retain analyte and for serving as a reaction chamber.

For all relevant aspects, the cavity may be adapted such that excitation light transmitted in the optical fibre to the cavity can excite a fluorophore within the cavity. The cavity may be adapted such that fluorescence emitted by the fluorophore can be transmitted in the optical fibre from the cavity to an outlet end of the optical fibre. The cavity may form part of the at least one microfluidic channel. The cavity may be a groove through a sheath of the optical fibre and into a core of the optical fibre. The optical fibre may project into the at least one microfluidic channel with the cavity being in the at least one microfluidic channel. The fluorophore may be fluorescein.

For all the above aspects, the optical fibre may form at least a part of a base of the at least one microfluidic channel. Excitation light transmitted in the optical fibre may be of a wavelength selected based on excitation wavelength of the fluorophore.

In accordance with a ninth preferred aspect there is provided a method of performing immunoassay using fluorescence, the method comprising the steps of providing an optical fibre in an immunoassay device having at least one microfluidic channel, the optical fibre comprising at least one cavity adapted to retain analyte and serve as a reaction chamber; passing a plurality of analytes along the at least one microfluidic channel at least one of the plurality of analytes containing a fluorophore; reacting the plurality of analytes in the at least one cavity; transmitting an excitation light in the optical fibre to the at least one cavity for exciting fluorophore in the cavity such that the fluorophore emits fluorescence; transmitting the emitted fluorescence along the optical fibre from the cavity to an outlet end of the optical fibre; and detecting the fluorescence.

The excitation light may be filtered at the detection to leave the emitted fluorescence. The excitation light and the emitted fluorescence may be transmitted in a direction parallel with the general direction of analyte flow in the at least one microfluidic channel. Wavelength of the excitation light may be selected based on the excitation wavelength of the fluorophore. The optical fiber may form at least a portion of a wall of the at least one microfluidic channel. The cavity may form part of the at least one microfluidic channel. The cavity may be a groove in the optical fibre. The fluorophore may be fluorescein.

BRIEF DESCRIPTION OF THE DRAWINGS

In order that the present invention may be fully understood and readily put into practical effect, there shall now be described by way of non-limitative example only preferred embodiments of the present invention, the description being with reference to the accompanying illustrative drawings.

In the drawings.

DETAILED DESCRIPTION OF THE PREFERRED EMBODIMENTS

Figure 1:
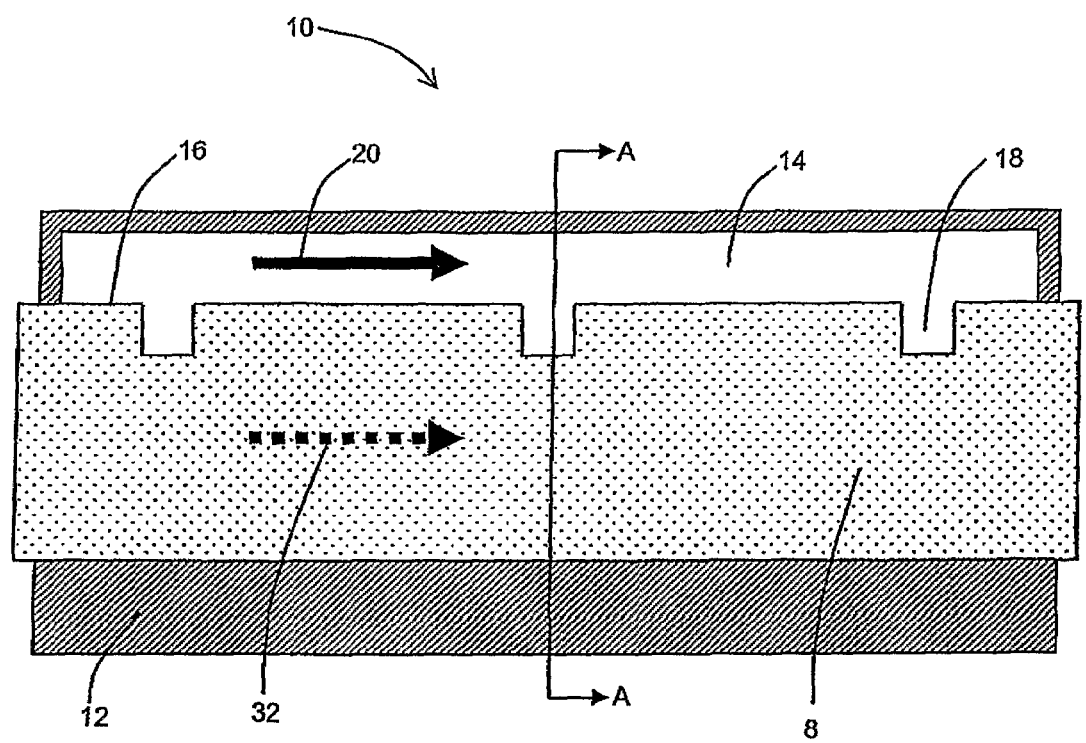
FIG. 1 is a schematic side view of an immunoassay device in accordance with one embodiment of the invention.
Figure 2:
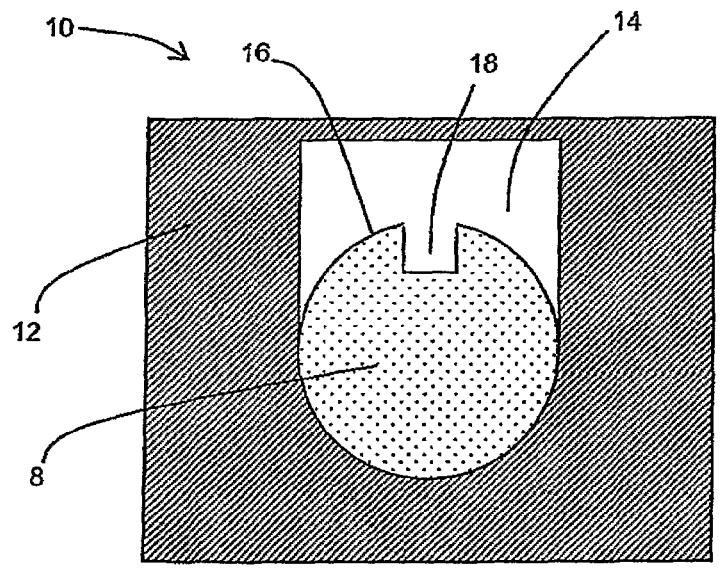
FIG. 2 is a sectional view at A-A of the immunoassay device of FIG. 1.
Figure 3:
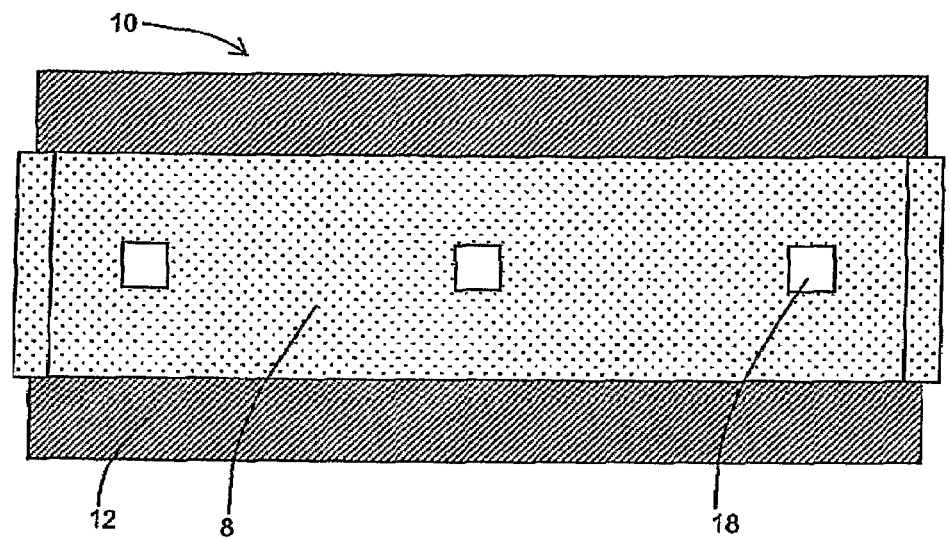
FIG. 3 is a plan view of the immunoassay device of FIG. 1.

According to one aspect, there is provided an optical fibre 8 for use in a fluorescence immunoassay device 10 as shown in FIG. 1, FIG. 2 and FIG. 3. The device 10 comprises a microfluidic substrate 12, which is typically made of a plastics material such as polymethyl-methacrylate (PMMA) sheets or polyester film, e.g. Mylar. The optical fibre is also typically made of PMMA, and has a core diameter of about 500 µm and cladding thickness of about 10 µm. PMMA is preferable for the optical fibre 8 due to its low fluorescence background noise compared to other types of polymeric fibres.

The device 10 includes at least one microfluidic channel 14 through which analyte can flow. The optical fibre 8 is embedded in the device 10 such that the optical fibre 8 forms at least a part of a wall 16 of the microfluidic channel 14. As shown, the optical fibre 8 forms the base of the microfluidic channel 14. It may form all or only part of the base. Along the length of the optical fibre 8 there is at least one cavity created in the optical fibre 8. Preferably, a plurality of cavities 18 is present. The cavities 18 open into and may form part of the microfluidic channel 14, and are grooves cut through the sheath of the optical fibre 8 and into the core of the optical fibre 8 using a $CO_2$ laser direct writing machine or an Excimer laser. Each groove is preferably about 100×100 µm wide and about 100 µm deep. Adjacent grooves are spaced about 1.5 mm apart. It is preferred for the optical fibre 8 to form the base of the microfluidic channel 14 so that the fluids will settle into the cavities 18 under gravity.

In a typical usage example of the immunoassay device 10, a first analyte containing a first antibody passes along through the microfluidic channel 14 in the general direction indicated by arrow 20. The cavities 18 capture and retain some of the first analyte. A second analyte containing an antigen of interest that is capable of binding with the first antibody is then passed along the microfluidic channel 14. Some of the antigen binds to the first antibody retained in the cavities 18. A third analyte containing a second antibody is subsequently passed along the microfluidic channel 14. The second antibody will have previously been labelled with a fluorophore, and is selected for its ability to bind with the antigen. Upon the third analyte passing along microfluidic channel 14, some of the second antibody binds with the antigen retained in the cavities 18. The cavities 18 thus serve as reaction chambers for the various analyte to interact, and ultimately to retain any fluorophore which can indicate the presence of the antigen.

Although it has been described that three different analytes are sequentially flowed in a typical process known as a "sandwich immunoassay", the device 10 can be used with any other immunoassay processes as long as it results in the fluorophore being retained in the cavities 18 in order to indicate the presence of a substance of interest that has been passed along the microfluidic channel 14.

Figure 4:
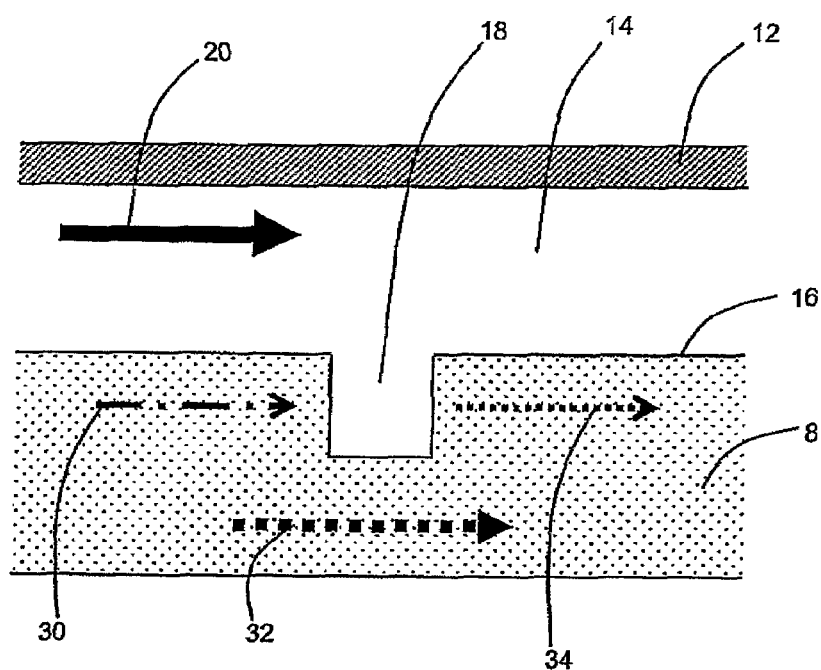
FIG. 4 is a close-up schematic side view of a cavity of the immunoassay device of FIG. 1.

The optical fibre 8 is adapted to transmit excitation light such as UV or visible light (indicated by arrows 30) from a broadband light source to the cavities 18. As can be seen in FIG. 4, the general direction of light transmission (arrow 32) is parallel to the general direction of analyte flow (arrow 20) in the microfluidic channel 14.

By appropriately tuning the wavelength of the excitation light such as by using an optical band-pass filter and an optical fibre probe, the fluorophore that has been retained in the cavities 18 will be excited by the excitation light and emit fluorescence. For example, if the fluorophore used is fluorescein with a peak excitation wavelength of around 490 nm, then a 470 nm±10 nm band-pass interference filter is appropriate. The emitted fluorescence is typically isotropic. Some of the emitted fluorescence will pass into microfluidic channel 14, and some (indicated by arrows 34) will pass into the optical fibre 8 and is transmitted to a light detector such as a photodiode at the outlet end of the optical fibre 8.

Since excitation of the fluorophores takes place within the cavities 18 of the optical fibre 8 itself, fluorescence emissions can be collected much more efficiently by the optical fibre 8 compared to external light detections systems involving lenses and mirrors. Using an optical fibre to transmit excitation light and collect emitted fluorescence also avoids the complicated process of scanning along the length of a channel in order to capture the total fluorescence emitted in the channel. Also, there is no "noise" due to fluorescence of the substrate. To collect the fluorescence from the cavities 18 will require the filtering of the source excitation light 32. The remaining signal is the fluorescence light 34.

By measuring the intensity of the detected fluorescence, the concentration of fluorophores can be proportionately determined. As the concentration of fluorophores is in turn proportional to the amount of substance of interest retained in the cavities 18, the concentration of the substance of interest can thus also be determined.

Figure 5:
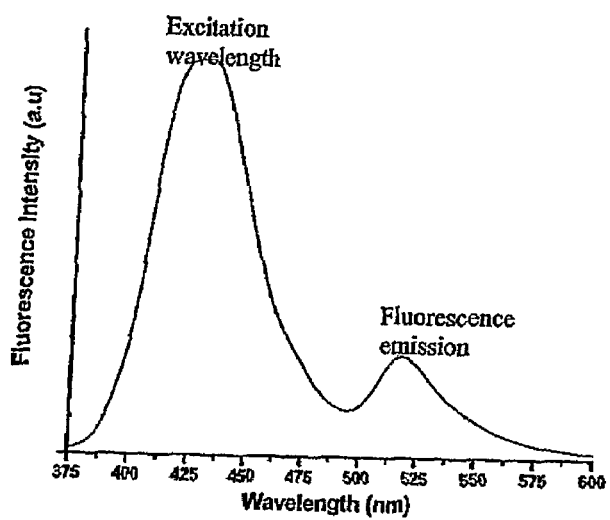
FIG. 5 is a graph of fluorescence intensity versus wavelength detected by a light detector when the immunoassay device of FIG. 1 is used.

FIG. 5 shows the fluorescence intensity detected by a light detector when 1 mg/l of fluorescein in a PBS buffer solution having a pH of 7.4 in the cavities 18 was excited by blue light having a wavelength of 430 nm from an LED source in an experimental verification of the device 10.

Because excitation light coming from the broadband light source is detected together with the fluorescence emitted by the fluoroscein in the cavities 18, it is preferable to have an optical filter at the end of the optical fibre before the light detector in order to clearly distinguish the excitation light from the fluorescence emission.

Light that is transmitted in the optical fibre 8 can be affected not only by the fluorophore in the cavities 18, but also by other factors such as microbending of the device 10. A reference light having a specially selected wavelength is thus preferably used as a control to compensate for light source fluctuations and losses and any other interferences that may arise from such other factors. Wavelength of the reference light may be outside the excitation and fluorescence emission spectrum of the fluorophore used. Wavelengths at red or infrared regions are generally suitable since most fluorophores do not fluoresce when exposed to light at these wavelengths. Since the fluorescence intensity is linearly proportional to the intensity of the excitation light, comparing the intensity of the reference light will allow for correction of the fluorescence intensity measured by the light detector.

Figure 6:
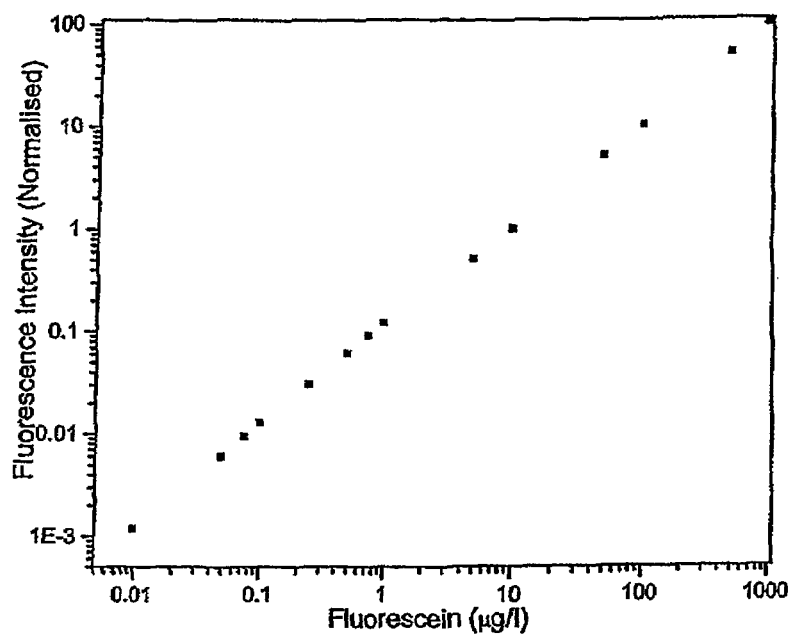
FIG. 6 is a graph of fluorescence intensity against fluoroscein concentration.

FIG. 6 shows that at low concentrations, the fluorescence intensity is linearly proportional to the concentration of fluorescein. This indicates that the device 10 is suitable for detecting not only the presence but also the concentration of a substance of interest in an analyte.

Figure 7:
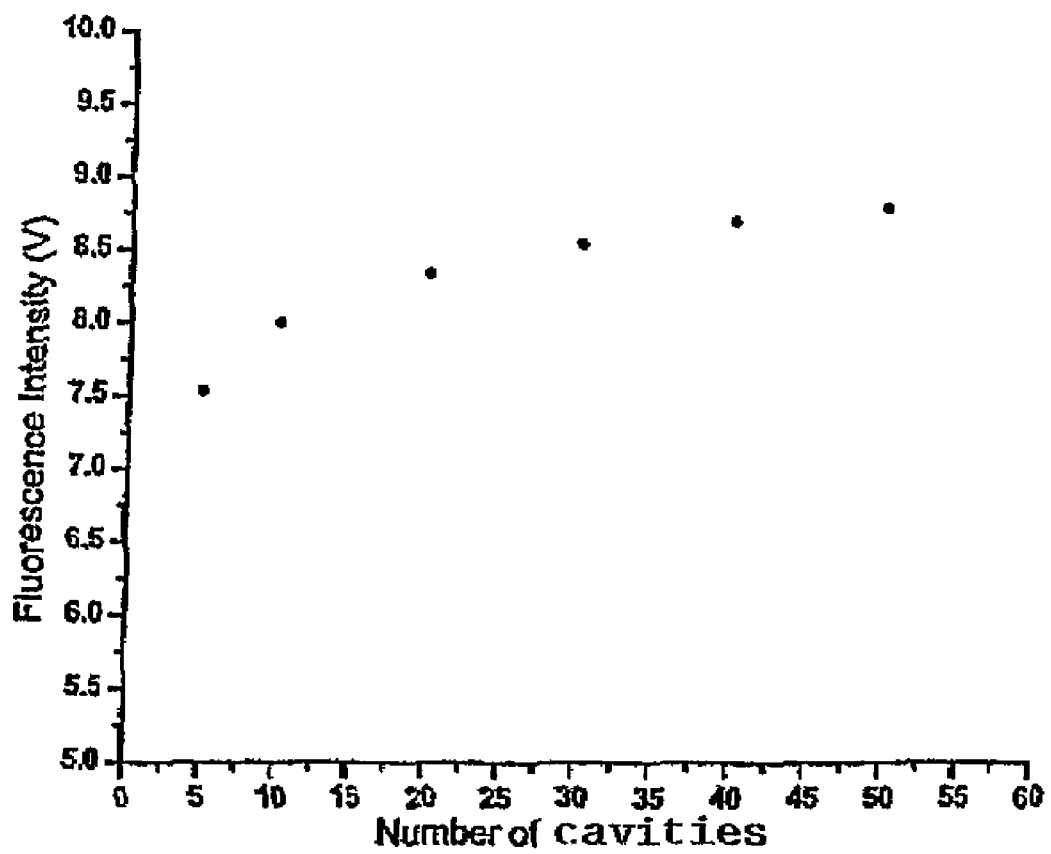
FIG. 7 is a graph of fluorescence intensity against number of cavities.

By experimental verification, it was seen that the number of cavities 18 along the optical fibre 8 affected the sensitivity of the immunoassay, as shown in FIG. 7. The intensity of fluorescence detected was found to be significantly affected by the number of cavities 18 at below thirty cavities. Beyond thirty cavities, there was no significant change to the intensity of the fluorescence detected. It is believed that by having a greater number of cavities 18, the majority of the substance of interest such as the antigen contained in the second analyte can be captured and retained by the cavities 18. As such, it is preferable to have at least thirty cavities 18 in order to maximise the sensitivity of the device during an immunoassay using a fluorophore such as fluorescein. For other fluorophores, sensitivity of the device can be optimised by optimising the number of cavities 18 accordingly.

The present invention is effective for a large range of fluorophores including, but not limited to those in Table 1 below.

TABLE 1

| Fluorophore | Excitation (nm) | Emission (nm) |
|---|---|---|
| 5-(hexadecanoyl) aminofluorescein | 497 | 519 |
| 5-hydroxytryptamine (HAT) | 370-415 | 520-540 |
| Acridine yellow | 470 | 550 |
| Acridine orange | 500 | 530 |
| Alexa Fluor 488 | 494 | 519 |
| Alexa Fluor 532 | 530 | 555 |
| Alexa Fluor 546 | 554 | 570 |
| BODIPY 500/510 | 508 | 515 |
| BODIPY 530/550 | 534 | 554 |
| Cascade Blue | 375 | 410 |
| Coumarin | 384 | 470 |
| CY2 | 489 | 506 |
| CY3 | 548 | 562 |
| CY5 | 650 | 670-700 |
| Dansyl | 340 | 520 |
| DAPI | 345 | 458 |
| DPH | 354 | 430 |
| Erythrosin | 529 | 554 |
| Ethidium Bromide | 510 | 595 |
| FITC | 494 | 518 |
| Fluorescein | 495 | 517 |
| FURA-2 | 340/380 | 500/530 |
| GFP | 395/489 | 509 |
| Hoechst 33258 | 365 | 480 |
| Hoechst 33342 | 355 | 465 |
| Laurdan | 364 | 497 |
| Lucifer yellow CH | 428 | 535 |
| Nile Red | 485 | 525 |
| Oregon Green 488 | 493 | 520 |
| Oregon Green 500 | 503 | 522 |
| Oregon Green 514 | 511 | 530 |
| Prodan | 361 | 498 |
| Pyrene | 341 | 376 |
| Rhodamine 110 | 496 | 520 |

TABLE 1-continued

| Fluorophore | Excitation (nm) | Emission (nm) |
|---|---|---|
| Rhodamine 123 | 505 | 534 |
| Rhodamine 6G | 525 | 555 |
| Rhodamine B | 540 | 625 |
| SITS | 336 | 438 |
| SNARF | 480 | 600/650 |
| Stilbene SITS, SITA | 365 | 460 |
| Texas Red | 589 | 615 |
| TOTO-1 | 514 | 533 |
| YOYO-1 | 491 | 509 |
| YOYO-3 | 612 | 631 |

Whilst there has been described in the foregoing description a preferred embodiment of the present invention, it will be understood by those skilled in the technology concerned that many variations or modifications in details of design or construction may be made without departing from the present invention. For example, the immunoassay device may comprise multiple microfluidic channels, each having an embedded optical fibre forming a channel wall. This allows different substances of interest to be tested using different fluorophores while minimising cross-talk problems since the excitation light for each channel is mostly confined to its own optical fibre.

We claim:

1. An optical fiber for use in an immunoassay device having at least one microfluidic channel, the optical fiber being for transmitting excitation light to the microfluidic channel and for transmitting emitted fluorescence to a light detector, wherein the optical fiber comprises at least one cavity, each cavity being adapted to retain analyte and for serving as a reaction chamber, wherein the at least one cavity opens into and forms part of the microfluidic channel and the at least one cavity is a groove through a sheath of the optical fiber and into a core of the optical fiber.

2. An optical fiber of claim 1, wherein the optical fiber is in a direction parallel with the general direction of analyte flow in the at least one microfluidic channel.

3. The optical fiber of claim 1, wherein the optical fiber forms at least a portion of a wall of the at least one microfluidic channel.

4. The optical fiber of claim 1, wherein the cavity is adapted such that excitation light transmitted in the optical fiber to the cavity can excite a fluorophore within the cavity.

5. The optical fiber of claim 4, wherein fluorescence emitted by the fluorophore is transmitted in the optical fiber from the cavity to an outlet end of the optical fiber.

6. The optical fiber of claim 4, wherein the fluorophore is fluorescein.

7. The optical fiber of claim 2 or 3, wherein the optical fiber projects into the at least one microfluidic channel with the cavity being in the at least one microfluidic channel.

8. The optical fiber of claim 1, wherein the optical fiber forms at least a part of a base of the at least one microfluidic channel.

9. The optical fiber of claim 4, wherein excitation light transmitted in the optical fiber is of a wavelength selected based on excitation wavelength of the fluorophore.

10. A method of performing immunoassay using fluorescence, the method comprising the steps of:
   a) providing an optical fiber in an immunoassay device according to claim 1, wherein the optical fiber comprises at least one cavity adapted to retain analyte and serve as a reaction chamber;

b) passing a plurality of analytes along the at least one microfluidic channel, wherein at least one of the plurality of analytes contains a fluorophore;

c) reacting the plurality of analytes in the at least one cavity;

d) transmitting an excitation light in the optical fiber to the at least one cavity for exciting the fluorophore in the cavity such that the fluorophore emits fluorescence;

e) transmitting the emitted fluorescence along the optical fiber from the cavity to an outlet end of the optical fiber; and f) detecting the fluorescence.

11. The method of claim 10, wherein the excitation light is filtered at the detection to leave the emitted fluorescence.

12. The method of claim 10, wherein the excitation light and the emitted fluorescence are transmitted in a direction parallel with the general direction of analyte flow in the at least one microfluidic channel.

13. The method of any one of claim 10, wherein the optical fiber forms at least a portion of a wall of the at least one microfluidic channel.

14. The method of any one of claim 10, wherein the cavity forms part of the at least one microfluidic channel.

15. The method of claim 10, wherein the fluorophore is fluorescein.

16. The method of claim 10, wherein the cavity is a groove in the optical fiber.

17. The method of claim 10, wherein wavelength of the excitation light is selected based on the excitation wavelength of the fluorophore.

18. An immunoassay device having at least one microfluidic channel, and at least one optical fiber according to claim 1.

19. An immunoassay device having at least one microfluidic channel, and at least one optical fiber according to claim 3.

20. The immunoassay device of claim 18, wherein the optical fiber is also for transmitting light to a light detector in a direction parallel with the direction of analyte flow.

21. The immunoassay device of claim 18, wherein the cavity is adapted such that excitation light transmitted in the optical fiber to the cavity can excite a fluorophore within the cavity.

22. The immunoassay device of claim 18, wherein fluorescence emitted by the fluorophore can be transmitted in the optical fiber from the cavity to an outlet end of the optical fiber and is detected by a light detector.

23. The immunoassay device of claim 18, wherein the fluorophore is fluorescein.

24. The immunoassay device of claim 18, wherein the cavity forms part of the at least one microfluidic channel.

25. The immunoassay device of claim 18, wherein the cavity is a groove through a sheath of the optical fiber and into a core of the optical fiber.

26. The immunoassay device of claim 18, wherein the optical fiber projects into the at least one microfluidic channel with the cavity being in the at least one microfluidic channel.

27. The immunoassay device of claim 18, wherein the optical fiber forms at least a part of a base of the at least one microfluidic channel.

28. The immunoassay device of claim 18, wherein excitation light transmitted in the optical fiber is of a wavelength selected based on excitation wavelength of the fluorophore.

29. An immunoassay device comprising the optical fiber of any one of claims 1 to 3.

* * * * *